United States Patent [19]
Heikkilä

[11] Patent Number: 5,632,279
[45] Date of Patent: May 27, 1997

[54] METHOD OF INTERFERENCE-TOLERANT TRANSMISSION OF HEARTBEAT SIGNALS

[75] Inventor: Ilkka Heikkilä, Oulu, Finland

[73] Assignee: Polar Electro Oy, Kempele, Finland

[21] Appl. No.: 464,658

[22] PCT Filed: Nov. 3, 1994

[86] PCT No.: PCT/FI94/00494

§ 371 Date: Jun. 15, 1995

§ 102(e) Date: Jun. 15, 1995

[87] PCT Pub. No.: WO95/12350

PCT Pub. Date: May 11, 1995

[30]  Foreign Application Priority Data

Nov. 4, 1993 [FI] Finland ................... 934877

[51] Int. Cl.⁶ ............................... A61B 5/0402
[52] U.S. Cl. ................... 128/696; 128/903; 607/60
[58] Field of Search ................. 128/696, 903, 128/706–710; 607/30, 32, 60

[56]  References Cited

U.S. PATENT DOCUMENTS

| | | |
|---|---|---|
| 4,625,733 | 12/1986 | Saynajakangas ............ 128/903 |
| 4,944,299 | 7/1990 | Silvian . |
| 4,958,645 | 9/1990 | Cadell et al. . |
| 5,058,581 | 10/1991 | Silvian . |
| 5,127,404 | 7/1992 | Wyborny . |
| 5,414,392 | 5/1995 | Schupak ............... 128/903 |
| 5,458,123 | 10/1995 | Unger ................. 128/903 |

FOREIGN PATENT DOCUMENTS

| | | |
|---|---|---|
| 0412424A3 | 2/1991 | European Pat. Off. . |
| 2907570A1 | 8/1980 | Germany . |

*Primary Examiner*—Jeffrey R. Jastrzab
*Attorney, Agent, or Firm*—Hoffmann & Baron

[57]  ABSTRACT

A method of interference-tolerant heartbeat measurement, in which method the heartbeat signal of a person is measured from a suitable part of the body and transmitted as burst signals from a transmitter (1-4) to a receiver (5-10) by telemetric data transmission, the transmitting interval of the burst signals being proportional to the measured heartbeat rate of the person. The burst signal is amplitude-modulated with a frequency or a frequency sequence characteristic of each transmitter/receiver unit, or a phase-shift sequence characteristic of each transmitte/receiver unit is caused in the burst signal at desired intervals, the receiver recognizing bursts intended for it on the basis of this sequence.

3 Claims, 3 Drawing Sheets

METHOD OF INTERFERENCE-TOLERANT TRANSMISSION OF HEARTBEAT SIGNALS

BACKGROUND OF THE INVENTION

The invention relates to a method of interference-tolerant heartbeat measurement, in which method the heartbeat signal of a person is measured from a suitable part of the body and transmitted as burst signals from a transmitting means to a receiver by means of talemetric data transmission, the transmitting interval of the burst signals being proportional to the measured heartbeat rate of the person.

Known telemetric transmitters of heartbeat measuring devices typically transmit a burst of about 5 kHz each time they have detected an ECG signal. The transmitting circuit consists of a simple resonance circuit, which is activated by means of transistor control. At certain intervals, for example at every fifth oscillation, a switch (transistor) in the transmitter closes and becomes conductive, whereupon the resultant current loads new energy into the magnetic field of the coil of the oscillating circuit. After a while when the switch opens, the current is switched off and the oscillating circuit is free for resonance vibration.

In heartbeat measurement, the transmitting unit transmits a signal each time the heart beats. The receiver counts the heartbeat rate on the basis of the time difference of successive transmitted signals. The method is in principle a method of time slot coding: the data to be transmitted is included in the transmission encoded in the time between the transmissions.

The known method described above is simple and reliable in circumstances free of interference. Individual disturbances may be filtered off by comparing the resultant heartbeat value to the previous results: if the new measurement result differs too much from the previous ones, it is probably caused by some external disturbance connected with the transmission/reception channel and may thus be eliminated from the measurement results.

However, if a wireless transmission of heartbeat data is performed in an environment with interference, the situation changes substantially. Thus a continuous irregular pulse sequence may arrive at the receiver, and it is difficult, often even impossible, to select the correct heartbeat signal from this sequence. Such a situation occurs easily when two or more users of heartbeat rate measurement devices are close to each other.

SUMMARY OF THE INVENTION

The purpose of this invention is to provide methods by means of which the aforementioned disadvantages are avoided and a simple coding of the heartbeat signal is achieved, so that the correct signals can be extracted from an incoming signal flow with interference in a reliable and exact manner without deteriorating the original accuracy of the timing of the signal.

In order to provide this, one embodiment of the method according to the invention is characterized in that the burst signal is amplitude-modulated with a frequency or a frequency sequence characteristic of the transmitter/receiver unit, on the basis of which the receiver recognizes bursts intended for it.

Another embodiment of the method according to the invention is characterized in that a phase-shift sequence characteristic of the transmitter/receiver unit is caused in the burst signal at desired intervals, the receiver recognizing bursts intended for it on the basis of this sequence.

A third embodiment of the method according to the invention is characterized in that the burst signal is amplitude-modulated with a number of different frequencies or frequency sequences, and that a number of different phase-shift sequences are caused in the burst signal at desired intervals, the receiver recognizing bursts intended for it on the basis of the combination formed by the amplitude modulation and the phase-shift sequences, the combination being individual to the transmitter/receiver unit.

Other preferred embodiments of the invention are characterized by what is disclosed in the appended claims.

The invention is thus based on one hand on the idea that the amplitude modulation caused by the control of the transmitting resonance circuit is clearly noticeable. When the frequency of the modulating signal is for example about 1 kHz, it is possible, by designing the receiver electronics in a suitable manner, to use the modulating signal to identify the correct heartbeat transmission in circumstances with interference. On the other hand, the invention is based on the idea that a phase shift of about 90 degrees occurs in the signal burst when the aforementioned switch is in a conducting state. This rapid phase change may be detected by using for example a phase lock technique. Each activation of the transmitting circuit may be provided either without the phase shift or by causing the phase shift with the accurate timing of the control. It is thus possible to include identification data of desired length in the transmission. By means of this method, it is possible to provide a fully encoded heartbeat transmission.

In the following, the invention will be described in greater detail by means of examples and with reference to the accompanying drawings, in which

DETAILED DESCRIPTION OF THE INVENTION

Figure 1:
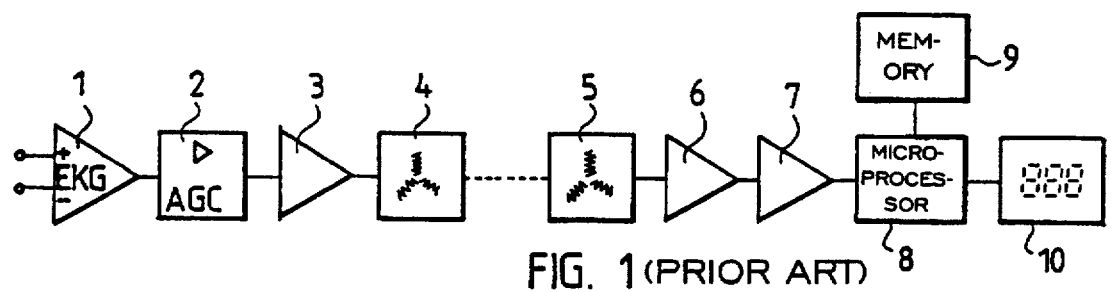
FIG. 1 is a block diagram of a known telemetric heartbeat measuring device, where the method according to the invention can be applied.

The electrodes (not described here) of the telemetric heartbeat measuring device shown in FIG. 1 are connected to the differential input terminals of an ECG preamplifier. A heartbeat signal supplied by the preamplifier 1 is amplified by an AGC amplifier 2, which controls a power amplifier 3, where the ac signal, i.e. the burst signal, of FIG. 2 controlling the coils 4 is provided. A magnetic field detected by receiver coils 5 is amplified in a sensitive preamplifier 6, whereafter the signal is applied to a signal amplifier 7. The output signal of the signal amplifier is processed in a microcomputer 8, which stores the heartbeat data counted in the measuring stage in a memory 9 and displays it on a liquid crystal display 10.

Figure 3:
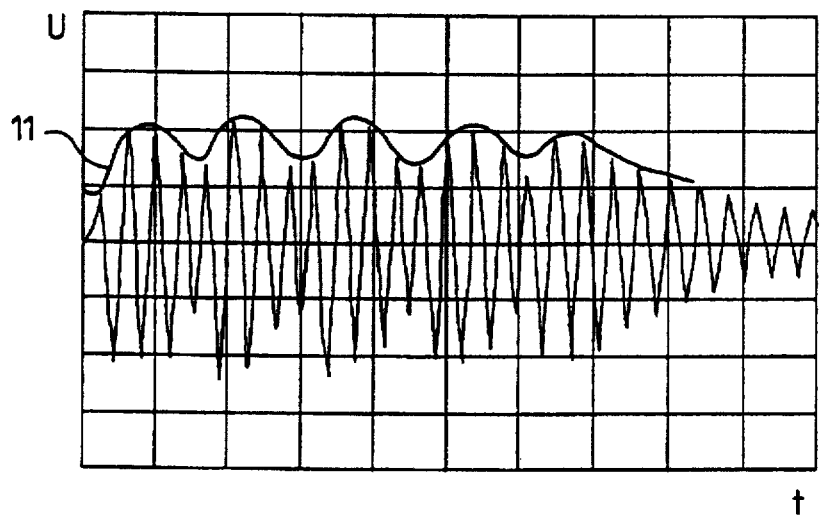
FIG. 3 shows one measured burst of the received burst signal in greater detail.

FIG. 3 shows the burst signal measured from the receiving circuit of FIG. 1 in greater detail. The amplitude modulation caused by the periodic control of the transmitting resonance circuit (formed by power amplifier 3 and transmitter coil 4) is clearly noticeable, and the modulating signal, the frequency of which is about 1 kHz, is outlined as an envelope 11 of the modulated signal of 5 kHz. By designing the receiver electronics in a suitable manner, it is possible to provide the identification of the correct heartbeat transmission even in circumstances with interference by using different frequencies in the modulating signal. In other words, according to the invention it is possible to provide an entirely receiver-specifically encoded heartbeat transmission by amplitude-modulating the burst signal with a frequency or frequency sequence characteristic of the transmitter/ receiver unit, on the basis of which the receiver recognizes the bursts intended for it on the basis of their particular modulation. The coding (see coding block 30 in FIG. 6) may be provided by means of for example an excitation sequence, which consists of five successive excitation pulses, the time intervals between the pulses forming an individual identification code.

Figure 4:
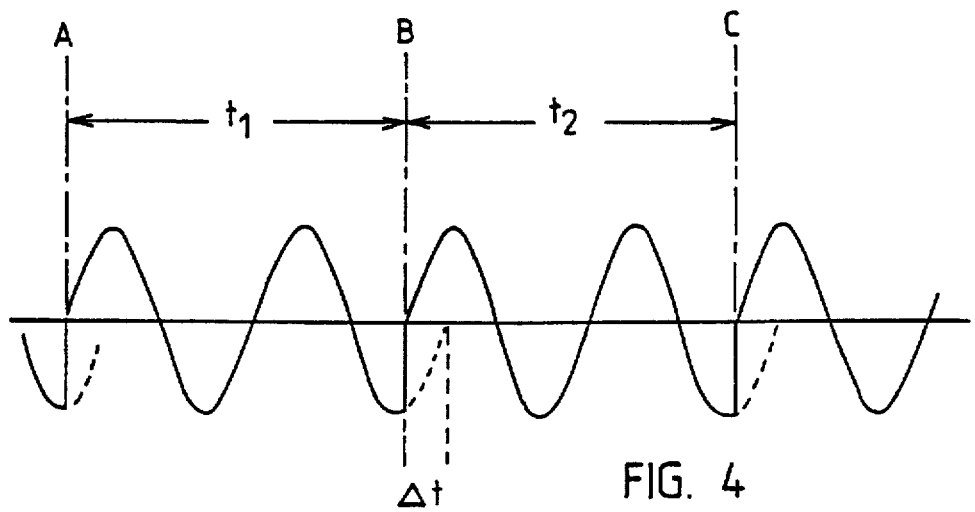
FIG. 4 shows the structure of the burst signal of FIG. 2 in still greater detail.

FIG. 4 shows the phase shift caused by the aforementioned forced control of the switch of the transmitting resonance circuit. The phase changes about 90 degrees. The rapid phase change may be detected by using for example a phase lock technique. Each activation of the transmitting circuit may be provided either without the phase shift or by causing the phase shift by means of the accurate timing of the control. Thus it is possible to include identification data of desired length in the transmission. It is possible to provide an entirely receiver-specifically encoded heartbeat transmission by causing, in the burst signal at desired intervals, a phase-shift sequence ABC, where t1=t2, characteristic of each transmitter/receiver unit, on the basis of which the receiver recognizes bursts intended for it on the basis of their phase-shift pattern.

It is also possible both to amplitude-modulate the burst signal with a different frequency or a frequency sequence and to cause different phase-shift sequences at desired intervals, the receiver being able to recognize bursts intended for it on the basis of the combination formed by the amplitude modulation and the phase-shift sequences.

It is clear for one skilled in the art that the different embodiments of the invention are not limited to the examples described above, but they may be modified within the scope of the appended claims.

What is claimed is:

1. A method of interference-tolerant heartbeat measurement, said method comprising the steps of:
   (a) measuring a person's heartbeat signal at a suitable part of said person's body;
   (b) forming burst signals corresponding to individual heartbeats of said heartbeat signal;
   (c) amplitude-modulating said burst signals with an identifier including at least one of:
      (i) a frequency; and
      (ii) a frequency sequence which are characteristic of a transmitter/receiver unit;
   (d) transmitting said burst signals, at a transmitting interval, from a transmitting means of said transmitter/receiver unit to a receiver of said transmitter/receiver unit by means of telemetric data transmission, said transmitting interval of said burst signals being proportional to a heartbeat rate corresponding to said person's measured heartbeat signal;
   (e) receiving said burst signals in said receiver; and
   (f) identifying said burst signals as emanating from said transmitting means on the basis of sensing said identifier so that said receiver recognizes those of said burst signals intended for it.

2. A method of interference-tolerant heartbeat measurement, said method comprising the steps of:
   (a) measuring a person's heartbeat signal at a suitable part of said person's body;
   (b) forming burst signals corresponding to individual heartbeats of said heartbeat signal;
   (c) causing a phase-shift sequence in said burst signals at desired intervals, said phase-shift sequence being characteristic of a transmitter/receiver unit:
   (d) transmitting said burst signals, at a transmitting interval, from a transmitting means of said transmitter/receiver unit to a receiver of said transmitter/receiver unit by means of telemetric data transmission, said transmitting interval of said burst signals being proportional to a heartbeat rate corresponding to said person's measured heartbeat signal;
   (e) receiving said burst signals in said receiver; and
   (f) identifying said burst signals as emanating from said transmitting means on the basis of sensing said phase-shift sequence so that said receiver recognizes those of said burst signals intended for it.

3. A method of interference-tolerant heartbeat measurement, said method comprising the steps of:
   (a) measuring a person's heartbeat signal at a suitable part of said person's body;
   (b) forming burst signals corresponding to individual heartbeats of said heartbeat signal;
   (c) amplitude-modulating said burst signals with a first identifier including at least one of:
      (i) a number of different frequencies; and
      (ii) a number of different frequency sequences;
   (d) causing a number of different phase-shift sequences in said burst signals at desired intervals, said phase-shift sequences forming a second identifier, said first and second identifiers forming a combination characteristic of a transmitter/receiver unit;
   (e) transmitting said burst signals, at a transmitting interval, from a transmitting means of said transmitter/receiver unit to a receiver of said transmitter/receiver unit by means of telemetric data transmission, said transmitting interval of said burst signals being proportional to a heartbeat rate corresponding to said person's measured heartbeat signal;
   (f) receiving said burst signals in said receiver; and
   (g) identifying said burst signals as emanating from said transmitting means on the basis of sensing said combination formed by said first and second identifiers so that said receiver recognizes those of said burst signals intended for it.

* * * * *

UNITED STATES PATENT AND TRADEMARK OFFICE
CERTIFICATE OF CORRECTION

PATENT NO. : 5,632,279
DATED : May 27, 1997
INVENTOR(S) : Heikkila

Figure 2:
FIG. 2 shows schematically a burst signal fed to the magnetic coils of the transmitting device of FIG. 1.

It is certified that error appears in the above-indentified patent and that said Letters Patent is hereby corrected as shown below:

<u>The Abstract, line 10,</u>  now reads "transmitte/receiver"; this should read --transmitter/receiver--;

<u>Column 2, lines 44-48,</u>  now reads "Figure 4 shows the structure of the burst signal of Figure 2 in still greater detail.

Figure 5:
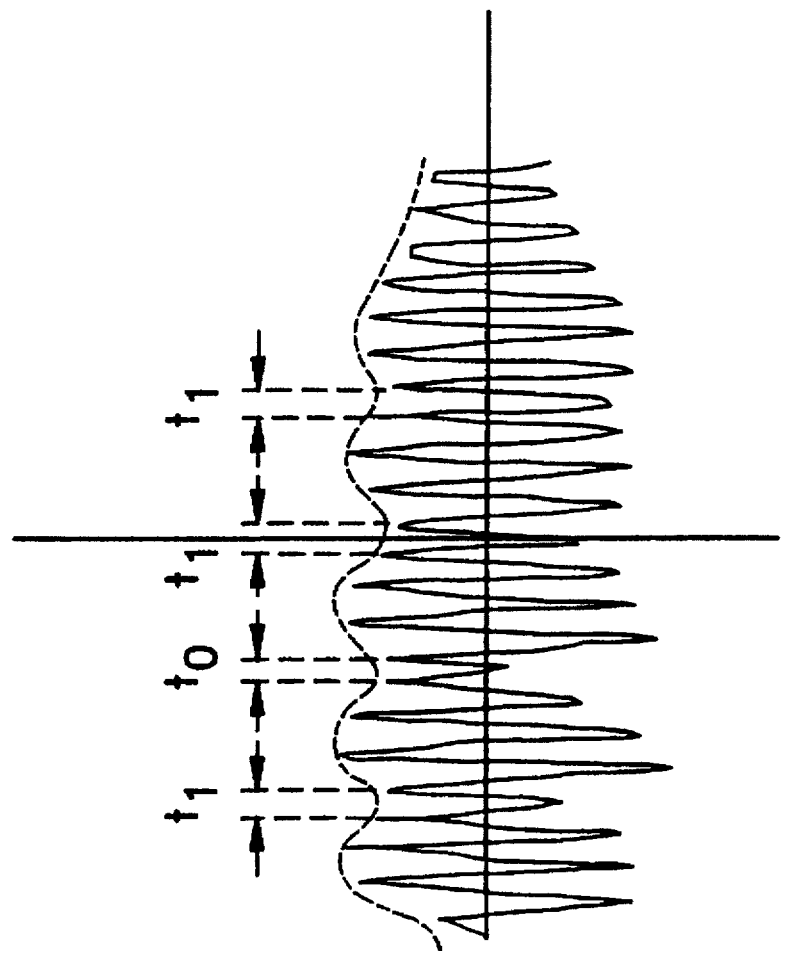
Figure 6:
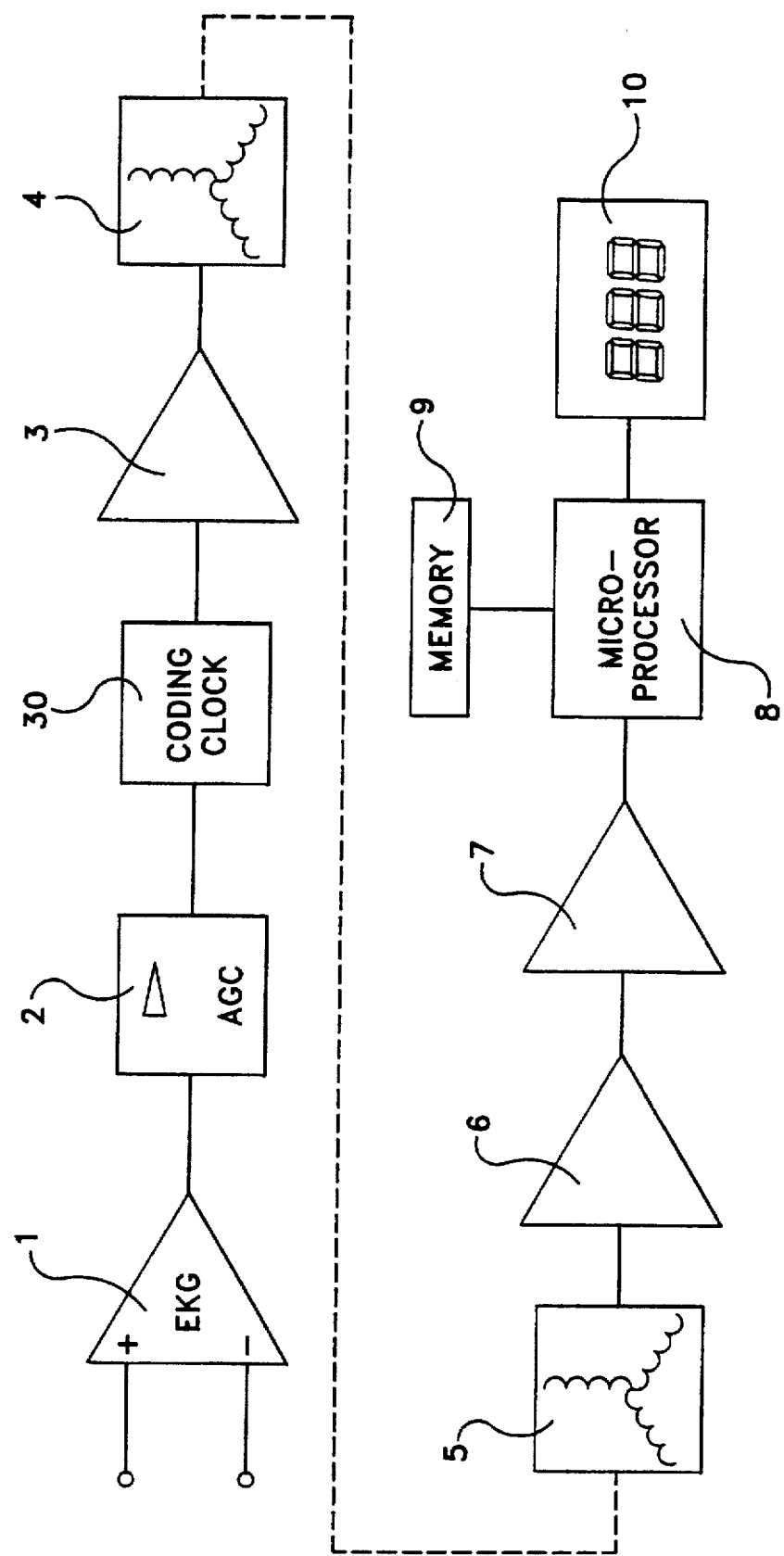

DETAILED DESCRIPTION OF THE INVENTION"; this should read --Figure 4 shows the structure of the burst signal of Figure 2 in still greater detail, Figure 5 shows the transmitted signal in combination coding; and Figure 6 shows the block diagram of Figure 1 modified for the present invention.

Signed and Sealed this

Sixteenth Day of September, 1997

*Attest:*

BRUCE LEHMAN

*Attesting Officer*   *Commissioner of Patents and Trademarks*